(12) United States Patent
Masiutin

(10) Patent No.: US 11,951,112 B2
(45) Date of Patent: Apr. 9, 2024

(54) METHOD OF TREATING LATE-ONSET CONGENITAL ADRENAL HYPERPLASIA DUE TO 21-HYDROXYLASE DEFICIENCY BY INDIVIDUALLY TAILORED GLUCOCORTICOID REGIMEN

(71) Applicant: Maxim Masiutin, Chișinău (MD)

(72) Inventor: Maxim Masiutin, Chișinău (MD)

(73) Assignee: Maxim Masiutin, Chisinau (MD)

( * ) Notice: Subject to any disclaimer, the term of this patent is extended or adjusted under 35 U.S.C. 154(b) by 312 days.

(21) Appl. No.: 17/590,784

(22) Filed: Feb. 1, 2022

(65) Prior Publication Data
US 2022/0323461 A1  Oct. 13, 2022

(30) Foreign Application Priority Data

Apr. 12, 2021 (MD) .................... md a 2021 0019

(51) Int. Cl.
*A61K 31/573* (2006.01)
*A23L 33/155* (2016.01)
*A23L 33/16* (2016.01)

(52) U.S. Cl.
CPC .......... *A61K 31/573* (2013.01); *A23L 33/155* (2016.08); *A23L 33/16* (2016.08)

(58) Field of Classification Search
CPC .................................................. A61K 31/573
See application file for complete search history.

(56) References Cited

U.S. PATENT DOCUMENTS

2017/0020877 A1  1/2017  Grigoriadis
2019/0231781 A1  8/2019  Grigoriadis

FOREIGN PATENT DOCUMENTS

| | | |
|---|---|---|
| AU | 2020207774 A1 | 8/2020 |
| AU | 2015209452 C1 | 11/2020 |
| CA | 2936974 A1 | 7/2015 |
| CN | 106102740 A | 11/2016 |
| CN | 111228274 A | 6/2020 |
| EP | 3096756 A1 | 11/2016 |
| IL | 246783 B | 10/2021 |
| IN | 201617026877 A | 8/2016 |
| JP | 2017503030 A | 1/2017 |
| JP | 2019081814 A | 5/2019 |
| JP | 2020138978 A | 9/2020 |
| KR | 20160106176 A | 9/2016 |
| MX | 2016009499 A | 2/2017 |
| NZ | 722122 A | 6/2020 |
| RU | 2718918 C2 | 4/2020 |
| RU | 2020112197 A | 5/2020 |
| WO | 2015112642 A1 | 7/2015 |
| WO | 2021016208 A1 | 1/2021 |

OTHER PUBLICATIONS

Phyllis W. Speiser et al., "Congenital Adrenal Hyperplasia Due to Steroid 21-Hydroxylase Deficiency: An Endocrine Society Clinical Practice Guideline" J Clin Endocrinol Metab, Nov. 2018, pp. 4043-4088, 2018.
Adina F Turcu et al., "Adrenal-derived 11-oxygenated 19-carbon steroids are the dominant androgens in classic 21-hydroxylase deficiency" European Journal of Endocrinology, 174, pp. 601-609, 2016.
Deborah P. Merke et al., "Congenital Adrenal Hyperplasia Due to 21-Hydroxylase Deficiency" The New England Journal of Medicine, 383;13, pp. 1248-1261, 2020.
Fotini-Heleni Karachaliou et al., "Cortisol response to adrenocorticotropin testing in non-classical congenital adrenal hyperplasia (NCCAH)" J Pediatr Endocrinol Metab, 29(12), pp. 1365-1371, 2016.
Sooyoung Chung et al., "Circadian rhythm of adrenal glucocorticoid: Its regulation and clinical implications" Biochimica et Biophysica Acta, 1812, pp. 581-591, 2011.
Emma K. Adam et al., "Diurnal Cortisol Slopes and Mental and Physical Health Outcomes: A Systematic Review and Meta-analysis", Psychoneuroendocrinology, Sep. 2017, pp. 1-40, 2017.
Thomas Dickmeis, "Glucocorticoids and the circadian clock", Journal of Endocrinology, 200, pp. 3-22, 2009.
C.E. Koch et al., "Interaction between circadian rhythms and stress", Neurobiology of Stress, Sep. 8, 2016, pp. 57-67, 2016.
Nicolas C. Nicolaides et al., "Stress-Related and Circadian Secretion and Target Tissue Actions of Glucocorticoids: impact on Health", Frontiers in Endocrinology, vol. 8, Article 70, pp. 1-11, 2017.
Peter C Hindmarsh et al., "Would Cortisol Measurements be a Better Gauge of Hydrocortisone Replacement Therapy? Congenital Adrenal Hyperplasia as an Exemplar", International Journal of Endocrinology, vol. 2020, Article ID 2470956, pp. 1-9, 2020.
Jordan Dimitrakov et al., "Adrenocortical Hormone Abnormalities in Men with Chronic Prostatitis/Chronic Pelvic Pain Syndrome", Urology, 71 (2), pp. 261-266, 2008.
Maria I. New, "Nonclassical 21-Hydroxylase Deficiency", The Journal of Clinical Endocrinology & Metabolism, 91 (11), pp. 4205-4214, 2006.

(Continued)

*Primary Examiner* — San Ming R Hui
(74) *Attorney, Agent, or Firm* — Bochner PLLC; Andrew D. Bochner

(57) ABSTRACT

A method of treating late-onset congenital adrenal hyperplasia due to 21-hydroxylase deficiency by individually tailored glucocorticoid regimen is provided. The method can be practically used to treat adult humans who suffer from symptoms of late-onset 21-hydroxylase deficiency caused by the mutation of the CYP21A2 gene. The method consists of daily intake of two glucocorticoids: dexamethasone in evenings and hydrocortisone in the mornings, in doses specially selected for each patient based on the analysis and monitoring of 17α-hydroxyprogesterone, progesterone, sex hormone-binding globulin, adre-nocorticotropic hormone, fasting glucose, hemoglobin A1C, C-Peptide, the Parathyroid Hormone intact, blood pressure, body weight. During glucocorticoid intake, in order to counterbalance ad-verse reactions, the patient should also take supplements of potassium, calcium, vitamin D and vitamin K.

16 Claims, No Drawings

(56) References Cited

OTHER PUBLICATIONS

Dana Badau et al., "Identifying the Incidence of Exercise Dependence Attitudes, Levels of Body Perception, and Preferences for Use of Fitness Technology Monitoring", International Journal of Environmental Research and Public Health, 15, 2614, pp. 1-20, 2018.
Walter L. Miller et al., "Tenascin-X, Congenital Adrenal Hyperplasia, and the Cah-X Syndrome", Hormone Research in Paediatrics, 89, pp. 352-361, 2018.
Helmuth-Günther Dörr et al., "Genotype-phenotype correlations in children and adolescents with nonclassical congenital adrenal hyperplasia due to 21-hydroxylase deficiency", Molecular and Cellular Pediatrics, pp. 1-7, 2020.
Sabina Baumgartner-Parzer et al., "EMQN best practice guidelines for molecular genetic testing and reporting of 21-hydroxylase deficiency", European Journal of Human Genetics, pp. 1341-1367, 2020.
Tania Mayvel Espinosa Reyes et al., "Molecular diagnosis of patients with congenital adrenal hyperplasia due to 21-hydroxylase deficiency", BMC Endocrine Disorders, pp. 1-8, 2020.
Wen-Hsuan Tsai et al., "Adrenal Tumor Mimicking Non-Classic Congenital Adrenal Hyperplasia", Frontiers in Endocrinology, vol. 11, Article 526287, pp. 1-5, 2020.
J. Homoki et al., "A Test for Heterozygocity of 21-Hydroxylase Deficiency", Annual Meeting of the European Society for Paediatric Research, Budapest, pp. 35-41, 1975.
Gideon Halperin et al., "Biosynthesis of Pregnanetriolone and Pregnanetetrol in Congenital Adrenal Hyperplasia", Acta Endocrinologica, pp. 439-451, 1967.
M. Zachmann et al., "Unusual Heterozygotes of Congenital Adrenal Hyperplasia Due to 21-Hydroxylase Deficiency", Acta Endocrinologica, pp. 557-565, 1978.
Dace L. Trence, "Management of patients on chronic glucocorticoid therapy: an endocrine perspective", Prim Care Clin Office Pract, pp. 593-605, 2003.
Siamak Moghadam-Kia et al., "Prevention and treatment of systemic glucocorticoid side effects", The International Society of Dermatology, pp. 239-248, 2010.
Emma Whittle et al., "Glucocorticoid Regimens in the Treatment of Congenital Adrenal Hyperplasia: A Systematic Review and Meta-Analysis", Journal of the Endocrine Society, vol. 3, Issue 6, pp. 1227-1245, 2019.
Ng SM et al., "Glucocorticoid replacement regimens for treating congenital adrenal hyperplasia (Review)", Cochrane Database of Systematic Reviews, Issue 3. Art. No. CD012517, pp. 1-48, 2020.
Robert L. Thunhorst et al., "Glucocorticoids increase salt appetite by promoting water and sodium excretion", AJP—Regul Integr Comp Physiol, vol. 293, pp. R1444-R1451, 2021.
Deborah Matthews et al., "What is the best approach to the teenage patient presenting with nonclassical Congenital adrenal hyperplasia: should we always treat with glucocorticoids?", Clinical Endocrinology, 78, pp. 338-341, 2013.
Marta Suminska et al., "Non-Classic Disorder of Adrenal Steroidogenesis and Clinical Dilemmas in 21-Hydroxylase Deficiency Combined with Backdoor Androgen Pathway. Mini-Review and Case Report", International Journal of Molecular Sciences, 21, 4622, pp. 1-16, 2020.
Selma Feldman Witchel et al., "Nonclassic Congenital Adrenal Hyperplasia", International Journal of Pediatric Endocrinology, vol. 2010, Article ID 625105, pp. 1-11, 2010.
Richard J. Auchus, "The backdoor pathway to dihydrotestosterone", Trends in Endocrinology and Metabolism, vol. 15 No. 9, pp. 432-438, 2004.
Duarte Pignatelli et al., "Androgens in Congenital Adrenal Hyperplasia", Hyperandrogenism in Women. Beyond Polycystic Ovary Syndrome. Front Horm Res. Basel, Karger, vol. 53, pp. 65-76, 2019.
Adina F. Turcu et al., "11-Oxygenated androgens in health and disease", Nature Reviews | Endocrinology, vol. 16, pp. 284-296, 2020.
Lise Barnard et al., "The A-ring reduction of 11-ketotestosterone is efficiently catalysed by AKR1D1 and SRD5A2 but not SRD5A1", Journal of Steroid Biochemistry and Molecular Biology, pp. 1-10, 2020.
Adina F. Turcu et al. "11-Oxygenated Androgens are Biomarkers of Adrenal Volume and Testicular Adrenal Rest Tumors in 21-Hydroxylase Deficiency", J Clin Endocrinol Metab, pp. 2701-2710, 2017.
Perrin C. White, "Update on diagnosis and management of congenital adrenal hyperplasia due to 21-hydroxylase deficiency", Current Opinion in Endocrinology, Diabetes and Obesity, vol. 25, No. 3, pp. 178-184, 2018.
Keisuke Nagasaki et al. "Foetal virilisation caused by overproduction of non-aromatisable 11-oxygenated C19 steroids in maternal adrenal tumour", Human Reproduction, vol. 35, No. 11, pp. 2609-2612, 2020.
Lise Barnard et al. "11-Oxygenated Estrogens are a Novel Class of Human Estrogens but Do not Contribute to the Circulating Estrogen Pool", Endocrinology, vol. 162, No. 3, pp. 1-11, 2021.
Kate C. Verbeeten et al. "The role of corticosteroid-binding globulin in the evaluation of adrenal insufficiency", J Pediatr Endocrinol Metab, pp. 107-115, 2018.
Shuhei Izawa et al. "A validation study on fingernail cortisol: correlations with one-month cortisol levels estimated by hair and saliva samples", The International Journal on the Biology of Stress, vol. 24, No. 6, pp. 734-741, 2021.
Ursula Turpeinen,"Determination of cortisol in serum, saliva and urine", Best Practice & Research Clinical Endocrinology & Metabolism, vol. 27, pp. 795-801, 2013.
L. Dolomie-Fagour et al., "Measurement of plasma free cortisol: an interest in resuscitation?", Ann Biol Clin, vol. 66, pp. 31-41, 2008.
Patricia Maidana,"Medición de Cortisol y Sus Fracciones Una Puesta Al Día", Medicina (Buenos Aires), vol. 73, pp. 589-584, 2013.
William E. Winter,"Cortisol ", Clinical Laboratory News, pp. 01-07, Sep. 1, 2012.
Matthew D Krasowski,"Cross-reactivity of steroid hormone immunoassays: clinical significance and two-dimensional molecular similarity prediction", BMC Clinical Pathology, pp. 01-13, 2014.
Neeti Agrawal et al.,"False elevation of serum cortisol in chemiluminescence immunoassay by Siemens Advia Centaur XP system in 21-hydroxylase deficiency: an 'endocrine laboma'", BMJ Case Rep., pp. 01-05.
Selim Kurtoğlu,"Non-Classical Congenital Adrenal Hyperplasia in Childhood", J Clin Res Pediatr Endocrinol, vol. 9, No. 1, pp. 01-07, 2017.
James M. Hawleya et al."Endogenous glucocorticoid analysis by liquid chromatography-tandem mass spectrometry in routine clinical laboratories", Journal of Steroid Biochemistry & Molecular Biology, vol. 162, pp. 27-40, 162.
Marco Cantu,"Clinical endocrinology and hormones quantitation: The increasing role of mass spectrometry", Minerva Endocrinologica, vol. 43, No. 3, pp. 261-284, Sep. 2018.
Arend-Jan Meinders et al., "Hoeveel water moeten we eigenlijk drinken?", Ned Magazine Health, pp. 1-3, 2010.
John S. Fuquaa et al.,"Neuroendocrine alterations in the exercising human: Implications for energy homeostasis", Metabolism Clinical and Experimental 62, pp. 911-921, 2013.

METHOD OF TREATING LATE-ONSET CONGENITAL ADRENAL HYPERPLASIA DUE TO 21-HYDROXYLASE DEFICIENCY BY INDIVIDUALLY TAILORED GLUCOCORTICOID REGIMEN

CROSS-REFERENCE TO RELATED APPLICATIONS

The present application claims priority pursuant to 35 U.S.C. § 119(a) to MD patent application 20210019, filed Apr. 12, 2021, which is incorporated by reference herein in its entirety.

BACKGROUND

This specification relates generally to medical science, namely, endocrinology. It can be applied to treat adults who suffer from the symptoms of late-onset congenital adrenal hyperplasia due to 21-hydroxylase deficiency (LOCAH21) caused by a mutation of the CYP21A2 gene in its on-classic form.

There is a known method of treating LOCAH21 with lifelong glucocorticoid therapy.[1] This treatment aims to suppress the adrenocorticotropic hormone (ACTH), which acts within the hypothalamic-pituitary-adrenal axis (HPA). Reduced ACTH reduces the secretion of glucocorticoid steroid hormones from adrenal cortex cells, especially in the adrenal glands' zona fasciculata. But the management and treatment of LOCAH21 with glucocorticoids is not straightforward. There is no standard approach, especially in drug selection and dosing. There are no established methods in monitoring the efficacy and the safety of the treatment. Overtreatment, i.e., long-term treatment with excessive glucocorticoid doses, can cause side effects. Such side effects are osteoporosis, hypertension, swelling, insulin resistance, dyslipidemia, obesity, potassium loss, to name a few. [4, 25, 26, 27] Excessive glucocorticoids may increase salt appetite by promoting water and sodium excretion but may also cause sodium retention but potassium excretion.[28] Undertreatment with glucocorticoids causes the symptoms to persist.

There is also a known method of treating signs and symptoms of hyperandrogenism of LOCAH21 in women, as an alternative to glucocorticoids, by oral contraceptive pills, [9, 30, 31] such as biphasic (estradiol/drospirenone) pill to block the ovarian source of androgens. There can also be administered such androgen blockers as spironolactone or cyproterone acetate.[3] Drospirenone is an agonist of the progesterone receptor and an antimineralocorticoid with antiandrogenic activity and no other important hormonal activity. Spironolactone blocks the effects of aldosterone and testosterone and has an effect similar to estrogen. It is an antimineralocorticoid and steroidal antiandrogen, as well as a potassium-sparing diuretic. The goal of treating LOCAH21 with oral contraceptive pills is to stimulate the hepatic sex hormone-binding globulin (SHBG), reduce serum free androgen, suppress HPA, and reduce ovarian androgen secretion. However, the suppression of the HPA also decreases the secretion of cortisol, synthesis of which is already impaired in LOCAH21. Besides that, in addition to the undesired diuretic effect, spironolactone may cause menstrual disturbances. Drospirenone has many side effects of its own and can cause breast cancer. As with glucocorticoid therapy, oral contraceptive pills have no standard approach in drug selection, dosing, and monitoring the efficacy. Also, the F2 gene (coagulation factor II, prothrombin), F5 gene (coagulation factor V, proaccelerin), CYP3A4, CYP2C9, CYP2C19 genes affect the metabolism of drugs that make up combined oral contraceptives. Mutations in these genes can lead to an increased or decreased concentration of drugs in the body after taking a standard dose, which affects the effectiveness of treatment or can lead to undesirable consequences in the form of an overdose.

There is also a known method of treating LOCAH21 with CRF1 receptor antagonists. Corticotropin-releasing factor (CRF) is a physiological regulator of the basal and stress-induced ACTH release (CRF is also known as corticotropin-releasing hormone). This method is described in patents AU2015209452, AU2020207774, CA2936974, CN106102740, CN111228274, EP3096756, IL246783, IN201617026877, JP2017503030, JP2019081814, JP2020138978, KR1020160106176, MX2016009499, NZ722122, RU0002718918, RU2020112197, US20170020877, US20190231781, WO2015112642, WO2021016208. [58-76] The examples of CRF1 receptor antagonists are Antalarmin hydrochloride, Pfizer CP 154526, CP 376395 hydrochloride, NBI 27914 hydrochloride, NBI 35965 hydrochloride, NGD 98-2 hydrochloride, Pexacerfont, R 121919 hydrochloride, SN003, 4-(2-chloro-4-methoxy-5-methylphenyl)-N-[(1S)-2-cyclopropyl-1-(3-fluoro-4-methylphenyl)ethyl]5-methyl-N-(2-propyn-1-yl)-2-thiazolamine (SSR-125543), or a pharmaceutically acceptable salt thereof. Secretion of CRF causes the release of ACTH from corticotropes in the anterior pituitary via binding to the CRF1 receptor, a member of the class B family of G-protein coupled receptors. Under the control of the hypothalamic corticotropin-releasing factor (CRF), the pituitary hormone ACTH stimulates steroidogenesis in the adrenal gland. Thus, the CRF1 receptor antagonists decrease ACTH secretion and hence decrease the secretion of cortisol, synthesis of which is already impaired in LOCAH21. Besides that, $CRF_1$ receptor antagonists are novel drugs that are not yet well studied. They are expensive and not yet widely available.

There is also a known method of treating LOCAH21 patients with hydrocortisone intake several times a day in a pattern that mimics natural cortisol secretion, but this method is inefficient. The main factor leading to this low efficiency is that conventional glucocorticoid therapy cannot reflect the rhythm of physiological cortisol. A new strategy consists of using hydrocortisone infusion pumps and oral modified-release hydrocortisone to replicate the cortisol rhythm has now been developed.[53] However, these infusion pumps or oral modified-release hydrocortisone are expensive and not widely available. Besides that, the infusion pumps provide inconvenience. Anyway, careful monitoring of the efficacy and adequacy of the doses selected in such treatment is still imperative. Cortisol replacement therapy attempts to mimic the normal circadian rhythm, but a single measurement per day does not provide information about the adequacy of replacement. The pulsation pattern of cortisol release, which is between 70 minutes and 90 minutes, will also affect the adequacy of the measurement. For available treatment modalities, achieving a normal plasma cortisol concentration distribution is a challenge. [10]

While other methods of treating LOCAH21 patients by glucocorticoids are based on monotherapy with just a single glucocorticoid, this leads to either overtreatment, like with long-lasting glucocorticoids that provide inadequately high glucocorticoid levels at night and disrupt circadian mechanisms even further but flattening the slope even more, or undertreatment as in case of short-lasting glucocorticoids, when ACTH suppression at night is insufficient.

In all existing methods previously described (except the one described in this invention), there is no emphasis on simultaneous careful monitoring of the doses based on exact parameters of efficacy (steroids) and safety (indicators of calcium and glucose homeostasis such as PTHI, C-Peptide, insulin) with simultaneous administration of calcium, vitamins D and vitamin K to avoid osteoporosis due to effect of glucocorticoids on calcium homeostasis, and with concurrent administration of potassium, to counterbalance increased potassium excretion due to mineralocorticoid effect of cortisol.

SUMMARY

The disclosed method solves the problem of high cost, low efficiency and side effects of other methods of treating LOCAH21. The embodiments provide cheap, efficient and safe treatment of LOCAH21, i.e., the non-classical form of late-onset of congenital adrenal hyperplasia caused by 21-hydroxylase deficiency due to mutation of the CYP21A2 gene.

LOCAH21 is an autosomal recessive disorder characterized by impaired cortisol synthesis, leading to variable degrees of postnatal androgen excess. Depending on the population, its prevalence is between 0.1% and 2%.[1] LOCAH21 is one of the most common autosomal recessive genetic diseases in humans.[2] LOCAH21 is caused by mutations in the CYP21A2 gene resulting in corresponding activity changes in the associated 21-hydroxylase protein enzyme, diminishing its catalytic activity towards its two substrates which are precursors to mineralocorticoids and glucocorticoids: progesterone and 17α-hydroxyprogesterone (17-OHP), therefore their concentrations rise, and they start to be used by other enzymes for androgen production. However, not all carriers of the mutations that lead to diminished 21-hydroxylase activity are symptomatic. Patients with LOCAH21 usually present with hyperandrogenism rather than glucocorticoid deficiency.[1] The impairment of cortisol synthesis is mild but clinically silent.[3] The total daily cortisol production in LOCAH21 patients may be about the same as in healthy controls.[4,5] However, changes in levels of cortisol from morning to evening, referred to as diurnal cortisol slopes,[6] are flatter in the patients than in healthy controls, which reflects and contributes to stress-related dysregulation of the circadian mechanisms, both central and peripheral. Such dysregulation has downstream effects on multiple aspects of biology, behavior, and health. It has both emotional and physical health outcomes. The effect size of flat slopes was most significant for immune and inflammation outcomes.[7, 8, 9] In healthy controls, plasma cortisol concentration in the early morning is on average 400-500 nmol/L, and 50 nmol/l around midnight. [10] Glucocorticoid and mineralocorticoid deficiency in LOCAH21 patients is sometimes mild enough to produce visible outcomes. That's why most patients, especially males, are asymptomatic.[1] Sometimes the symptoms are very light and common to other illnesses. Therefore, most patients never receive the diagnosis of LOCAH21. More than 200 pathogenic or likely pathogenic variants have been identified in the CYP21A2 gene, leading to various forms of 21-hydroxylase deficiency, which can cause highly variable signs and symptoms or may not cause any symptoms at all.[11] The difference in residual enzyme activity of various alleles explains the different degrees of severity of the disease. Therefore, there are multiple forms of congenital adrenal hyperplasia caused by 21-hydroxylase deficiency. The classical form, with about 2% enzyme function or less, occurs in approximately 1 in 15 000 births globally. In contrast, the non-classical form is the mildest and late-onset one, usually retaining about 20% to 50% of enzyme function.[1] The present invention aims to treat only the disease's non-classical late-onset form in adults.

Women may experience various symptoms, such as hirsutism, oligomenorrhea, infertility, polycystic ovary, and male pattern baldness.[1] During the follicular phase, progesterone accumulates with 17-OHP, which thins the endometrium and changes the cervical mucus (such as progestogen contraceptives), which can lead to oligomenorrhea or amenorrhea. Therefore, when evaluating oligomenorrhea or amenorrhea and infertility, LOCAH21 is sometimes spontaneously diagnosed. However, about 90% of women with LOCAH21 have never received a diagnosis. Once attempting to conceive, approximately 83% of LOCAH21 women become pregnant within a year, with or without glucocorticoid therapy. However, such women have an increased risk of miscarriage. [3] Males with LOCAH21 may present with early balding, chronic prostatitis, chronic pelvic pain syndrome, and testicular adrenal rest tumors. [1, 12, 13] All patients, regardless of sex, may present with acne, fatigue, hypotension, abdominal pain, muscle or joint pains, irritability, and psychiatric vulnerability. [1, 3]

There are many different mutations of the CYP21A2 gene and high variability of signs and symptoms of 21-hydroxylase deficiency. Therefore, the management and treatment of LOCAH are case-specific.[14] The functional CYP21A2 gene is located close to the non-functional pseudogene CYP21P1. The high sequence similarity between them indicates that these two evolved in tandem through the intergenic exchange of DNA. The CYP21A2 gene is located in the RCCX cluster, the most complex gene cluster in the human genome. [15] The mutations associated with LOCAH21 may be caused by deletions of the CYP21A2 gene, small gene conversion, duplication of CYP21A1P pseudogene, and duplication of C4B gene, as well as by other factors like copy number variations of the entire RCCX cluster and simple-nucleotide polymorphisms. [16] Due to increased homology between the CYP21A2 gene and the CYP21A1P pseudogene, and the complexity of the locus, it isn't easy to study the gene at the molecular level by sequencing and obtain solid, conclusive results. [17] Not all disease-causing mutations have been well studied.[18] That is why the treatment of LOCAH21 cannot be performed based on genetic analysis alone. Therefore, treatment should be is specific to each situation.

The details of one or more embodiments of the subject matter of this specification are set forth in the accompanying drawings and the description below. Other features, aspects, and advantages of the subject matter will become apparent from the description, the drawings, and the claims.

DETAILED DESCRIPTION

The disclosed treatment method consists of a daily intake of two glucocorticoids. The first glucocorticoid is a long-lasting one—dexamethasone—taken once daily in the evening (at night) immediately before going to sleep, but no later than 11 PM. Dexamethasone should preferably be taken with a meal for those who eat in the evenings, but not earlier than 7 PM. The second glucocorticoid is short-lasting—hydrocortisone—taken once daily in the morning on wake up, but not earlier than 5 AM. For those who take breakfast at least one hour after waking up, hydrocortisone should preferably be taken with a meal. But in no case should it be aimed to be taken in more than one hour after wake up, i.e., it must be taken no later than one hour after wake up. However, if a dose is skipped because of being forgotten, it should be taken immediately when figured out, but, for hydrocortisone, not later than 5 PM. Besides glucocorticoids, the following substances should be taken daily to counteract glucocorticoid side effects: potassium supplements of 4 g of elemental potassium daily split to at least three intakes, calcium supplements of 1.4 g of elemental calcium daily divided into at least three intakes, vitamin D3 supplements daily 1000 IU, Vitamin K supplements daily 150 mcg, and pure, clean water of at least 0.5 liters per day, but preferably 2 liters per day.[51, 54, 55] The supplements mentioned above should be taken regardless of the values of these minerals and vitamins taken with food.

The adjustment of the dose of glucocorticoids is based on the measurements of the following parameters: SHBG, 17-OHP, progesterone, C-peptide, PTHI, fasting glucose, insulin, hemoglobin A1C, blood pressure, and weight. These measurements should be done before starting glucocorticoid therapy and then regularly, twice monthly for men and postmenopausal women and once a month on day 3 for women who have periods. After two months of obtaining optimal results, measurements should be done once in three months for one year and then two times a year since then.

The initial dose is 0.25 mg of dexamethasone and 10 mg of hydrocortisone taken as described above. The goal of the treatment is to provide ACTH suppression to reach desired values of 17-OHP, progesterone, and SHBG. During the treatment, 17-OHP for women should be less than 0.8 ng/mL who have periods, and less than 0.5 after menopause, and for men less than 1.6. Progesterone for women should be less than 2.7 nmol/L who have periods, less than 0.3 after menopause, and for men less than 0.4. SHBG for women should be between 27 and 120 nmol/L. For men of age before 49, SHBG should be between 18 and 50 nmol/L, and for men of age 50 or older, SHBG should be between 20 and 70 nmol/L.

To monitor for possible overtreatment, the following parameters should be checked: ACTH should be more than 7 pg/mL, fasting glucose should less than 5.54 mmol/L, hemoglobin A1C less than 6%, insulin should be more than 2.6 μU/mL, C-Peptide should be less than 4.4 ng/mL, PTHI should be less than 65 pg/mL. If one of the parameters mentioned in this paragraph violated the limit indicated here, then the dexamethasone dose should be decreased by half, and so on each time until the values will normalize. The minimal dose of dexamethasone is 0.05 mg. If even a lower dose is required, the dexamethasone should be discontinued, and the patient should only take hydrocortisone. To monitor the adequacy of the treatment, if the values of 17-OHP, progesterone and SHBG did not reach target values defined by this invention, and the other values described in the previous paragraph do not violate the limits set there, then the dexamethasone dose should be increased in 0.25 mg increments, but up to the following limitation: in no case the daily dose should be more than 0.75 mg. If the goal is achieved with a lower dose of dexamethasone, the lowest possible amount should be used, provided that 17-OHP, progesterone, and SHBG do not exceed the limits described in the previous paragraph.

If all the monitored values normalize except the blood pressure, which is low, then the daily value of hydrocortisone should be increased in 5 mg increments to raise blood pressure to normal. However, the total daily amount of hydrocortisone should not exceed 30 mg. Doses larger than 10 mg should not be taken at once. They must be split and taken no more than 10 mg at once, with the interval of two hours. The last dose should be the smallest, if not split evenly by 10. If the amount of hydrocortisone is already 30 mg and the blood pressure is still low, then the patient should slightly but gradually increase sodium intake. Still, no more than 2000 mg of elemental sodium daily in total, providing it would not cause swelling.

If blood pressure rises above normal value, or swelling occurs, then the patient should decrease the daily amount of total sodium intake (the primary source of it is the salt sodium chloride) to 400 mg of elemental sodium, which is equivalent to 1 g of salt. Sodium in food and water should also be taken into consideration. If reducing sodium still does not help to reduce swelling or decrease the blood pressure back to normal in five days, then the dose of hydrocortisone should be decreased in 10 mg decrements down to 10 mg, and then in 2.5 mg decrements down to 2.5 mg until swelling (if any) stops and the blood pressure normalized (if it was high). If blood pressure is still high or swelling still presents, then the patient should stop taking glucocorticoids, stop the treatment described here altogether and apply to a nephrologist to check kidney function. If the dose of hydrocortisone that does not cause high blood pressure or swelling is 5 mg or less, then the patient should switch from hydrocortisone to prednisolone using the conversion rate of one mg of prednisolone to 5 mg of hydrocortisone, and try to gradually raise the amount of prednisolone to 2 mg (the equivalent of 10 mg of hydrocortisone). Prednisolone should always be taken in one daily dose without a split.

If bodyweight increases, the patient has to reduce daily calory intake, take regular physical exercises if not doing so, and gradually increase the exercise's duration and intensity until the weight is not restored.

If hydrocortisone is not available, the patient can use prednisolone using the same techniques as for hydrocortisone described in this invention. However, the dosage of prednisolone should be different. The conversion rate is one mg of prednisolone equals to 5 mg of hydrocortisone.

The aims of the method described in this invention are to lower the treatment cost, exclude side effects caused by treatment with other methods, and provide better treatment outcomes. All substances in this treatment method are administered orally. This method involves testing the levels of certain hormones. For this purpose, the way to take the biological material is to extract venous blood.

The method described in the present invention has several advantages.

First, the present method does not rely on expensive liquid chromatography-tandem mass spectrometry (LC-MS/MS) and can use immunoassays to measure steroids for analysis needed to tailor patient-specific regimens and doses. Besides steroid measurement, it is based on the measurements of some other essential indicators to avoid complications of overtreatment. These measurements also help prevent undertreatment. Consequently, an advantage of this method is that cheap immunoassays are enough for the method, without the need to use expensive LC-MS/MS.

Second, the present method is based on administering the specially tailored dose of a group of glucocorticoids. Such administration has two goals. The first goal of glucocorticoid administration is to suppress ACTH just enough to eliminate androgen excess.[1] The second goal of glucocorticoid administration is to provide an adequate daily-variable intake of agonists of glucocorticoid and mineralocorticoid receptors in a pattern close to diurnal slopes to avoid complications associated with the flat slope mentioned above. Hence, an advantage of this method is the reliance on administering exogenous steroids, which are very cheap. Another advantage is that these steroids were approved for medical use many decades ago, thus are well studied.

Third, the present method is based on administering substances that counteract the effects of higher levels of glucocorticoid receptor agonists at night due to glucocorticoid administration than such levels are in healthy people. Such higher levels are needed to provide continuous ACTH suppression to avoid excessive progesterone and 17-OHP accumulation during the night.

Fourth, the present method does not rely on androgen measurement because of the low practical utility of such measurements. The androgen backdoor pathway is a collective term for all metabolic pathways, where clinically relevant androgens are synthesized with the roundabout of testosterone as an intermediate product. This pathway was initially described in 2004 as the pathway by which 5α-reduction of 17-OHP finally leads to 5α-dihydrotestosterone. [32] Since 2016, several other metabolic routes have been discovered and described, which lead to 11-oxygenated androgens, which are very potent agonists of androgen receptors. The backdoor pathway is an alternative to the conventional androgenic pathway involving testosterone. The backdoor pathway is not always considered in the clinical evaluation of patients with hyperandrogenism. [33, 34, 35, 36, 37] Due to high levels of unconventional androgens, which can present amid the normal testosterone levels, ignoring this pathway may lead to diagnostic pitfalls and confusion. Besides that, unlike conventional androgens such as testosterone and androstenedione, the androgens produced by the backdoor pathway, namely 5α-dihydrotestosterone and 11-oxygenated androgens, are not converted into estrogens by aromatase in vivo.[38, 39]

Fifth, an additional advantage of the present method is that it does not rely on cortisol measurement. Cortisol is lipophilic and is transported across the body in such a form that it is bound to albumin and to corticosteroid-binding globulin, also known as transcortin. Only a small part of the total serum cortisol is unbound and has biological activity. [40] The measurement of cortisol is prone to complexity, high cost to achieve adequate precision in LOCAH21 patients, and low diagnostic value. Cortisol is produced in a pulsatile and diurnal pattern and has a short half-life. [41, 42, 43, 44] The pulse frequencies of cortisol release are between 70 and 90 minutes. [10] Besides that, using immunoassays like radioimmunoassay (MA), chemiluminescent immunoassay (CLIA), electrochemiluminescence immunoassay (ECLIA) to measure cortisol is prone to cross-reactivity with structurally similar molecules.[45, 46, 47] The examples of endogenous compounds structurally related to cortisol are 6β-hydroxycortisol and 21-deoxycortisol. Since 21-deoxycortisol may be at a high level in LOCAH21 and has a similar structure to cortisol, it can cross-react in immunoassays, which will cause errors in interpreting the results, i.e., showing normal or high cortisol values when the true cortisol is actually low. Since the immunoassays may cross-react due to interactions with structural analogs, and the selectivity provided by LC-MS/MS has primarily overcome these limitations, the use of LC-MS/MS instead of immunoassay in cortisol measurement aims to provide higher specificity. [48, 49, 50] However, LC-MS/MS has the disadvantages of higher cost and lower availability compared with immunoassays.

The present method is based on the administration of two glucocorticoids. The first one, long-lasting, the dexamethasone, is needed for ACTH suppression, especially at night, and is taken in lower doses at night to not contribute to the flat cortisol slope. The second one, short-lasting, hydrocortisone, taken in the morning in a higher dose to mimic the morning concentration of cortisol in healthy controls and improve the diurnal biological cycles. Hydrocortisone is a medication that has the same molecule as endogenous cortisol. Unlike dexamethasone, which has no mineralocorticoid activity, cortisol is also a mineralocorticoid receptor agonist. Cortisol has a wide range of effects. Such effects include changes in carbohydrate, protein and lipid metabolism, catabolism of the skin, muscles, connective tissue and bone; immune regulation, blood pressure and circulatory system regulation; influence on mood and central nervous system function, and influence on the regulation of circadian rhythm mechanisms.[52] That's why lack of morning cortisol, i.e., the flatter daily cortisol curve in LOCAH21 patients leads to bad outcomes, and supplementation of exogenous morning cortisol is beneficial. Although exercise, particularly sustained aerobic activity, is a potent stimulus of cortisol secretion, [52] but due to an insufficient 21-hydroxylase function in LOCAH21 patient, such aerobic activity may not always lead to higher cortisol secretion, so morning supplementation of cortisol is necessary.

The diagnostic criteria for the LOCAH21 patients eligible for the treatment using the method described in this invention are the following. In women before menopause, all hormone analysis should be done on day 3 of the menstrual cycle. If this day falls on a date when the person who takes samples for analysis is not available, i.e., because of a weekend or holidays, it can be done on subsequent days, but not more than day 6 of the cycle. If there were no periods for at least three months in women with amenorrhea, samples for analysis could be taken on any day. All the samples should be taken in the early morning, at the same time, preferably at 8 AM or 7 AM. To be diagnosed as a LOCAH21 patient for the aim of treatment by the current method, a patient needs to have one or more of the following: 17-OHP of more than 1.7 ng/mL for women or 2.2 for men; SHBG of more than 128 for women or 55 for men before 49 years old or 77 for men of 50 years old or older; progesterone of more than 4.0 nmol/L for women or 0.7 for men. If a woman has just SHBG alone elevated or progesterone alone elevated with the other two parameters being in the normal range, then it is not sufficient to confirm the LOCAH21 diagnosis, and additional analysis of 21-deoxycortisol (>5.0 ng/dL) and/or 11-deoxycortisol (<0.3 μg/l) is necessary to confirm the diagnosis. In the case of borderline values, at least two subsequent tests are required to finally rule the diagnosis: for men and postmenopausal women the tests should be done one week apart, for women who have periods—on day 3 of the next period. Complete sequencing of the CYP21A2 gene may be performed. Still, it is not required for the present treatment method, since its diagnostic value is low due to a large number of unknown variants and the complexity of the locus, but the cost of the sequencing is high.[16, 17, 18] However, genetic testing can be used to rule out false positive diagnoses based solely on biochemical parameters, even with ACTH stimulation, because elevated 17-OHP levels may also be caused by ovarian or adrenal tumors rather than mutations in the CYP21A2 gene. [19] Anyway, other diagnostic tools may be used to exclude ovarian or adrenal tumors like ultrasound or computer tomography scans. In the case of borderline values, as an alternative, the steroids described in the current paragraph can be measured within an ACTH stimulation test [1, 56, 57] if the injectable of synthetic ACTH medication is available. One of the benefits of the ACTH stimulation test is to distinguish steroids of adrenal origin from steroids of gonadal origin. Another option is to test levels of pregnanetriolone in 21 h urine. There is little or no excretion of pregnanetriolone in the urine of healthy people. In patients with LOCAH21, the daily excretion exceeds 100 µg, but ACTH stimulation will further increase the excretion.[0, 21, 22, 23]

The eligibility criteria for the LOCAH21 patients suitable for the treatment using the present method are the following. A patient has to be at least eighteen years old. Besides that, the patient does not have to be pregnant. Besides that, the patient should not have a systemic fungal infection, uncontrolled hyperglycemia, diabetes mellitus, glaucoma, joint infection, uncontrolled hypertension, herpes simplex keratitis, varicella infection, swelling, or diminished renal function. The patient should also have a normal blood glucose level on the glucose tolerance test (GTT). For instance, for a 2-hour GTT with 75 g intake, a glucose level should be below 7.8 mmol/L. Other parameters should also be checked in another day from the GTT. Fasting glucose levels should be between 3.33 and 5.54 mmol/L. Hemoglobin A1C should be between 4 and 6%. Insulin should be between 2.6 and 24.9 µU/mL. C-Peptide should be between 1.1 and 4.4 ng/mL. The intact Parathyroid Hormone (PTHI) should be between 15 and 65 pg/mL.

The concrete embodiments of the present invention, i.e., the implementation examples, are the following.

A female patient of age 25 has three rare CYP21A2 variants: rs114414746 AG (global "A" allele frequency is 0.695%), rs150697472 CT (global "T" allele frequency is 1.224%), rs545719209 AG (global "G" allele frequency is 0.648%). The patient presented with acne, painful menstruation lasting on average seven days, ovarian cysts of up to 9 mm in diameter, vaginal candidiasis (white curd-like vaginal discharge), and morning fatigue. The analysis results before starting the treatment were the following: 11-deoxycortisol↓ 0.12 µg/l (reference range 0.5-3.0), 17-OHP↑ 1.87 ng/mL (reference range 0.1-0.8), progesterone 0.47 nmol/L (reference range 0.181-2.84), SHBG 65.64 nmol/L (reference range 32.4-128), ACTH 24.89 pg/mL (reference range 7.2-63.3), PTHI 32.6 pg/mL (reference range 15-65), C-Peptide 1.81 ng/mL (reference range 1.1-4.4), glucose 4.46 (4.1-5.9 mmol/L), Hemoglobin A1C 5.0% (reference range 4-6%), insulin 11.4 µU/mL (reference range 2.6-24.9 µU/mL), GTT 75 g after 2 hours: 5.51 mmol/l, blood pressure—120/80, weight—70 kg. After three months of treatment with 0.125 mg of dexamethasone and 2 mg of prednisolone daily, the results were the following. Vaginal candidiasis resolved without any fungicide medication. There was no more vaginal discharge. Morning fatigue resolved, acne resolved, menstruation became painless, and duration decreased to an average of 4 days. Ovarian cysts decreased in size to a maximum of 3 mm. All serum tests were in the normal reference range. 17-OHP decreased to 0.72 ng/mL, progesterone decreased to 0.31 nmol/L, SHBG decreased to 36.9 nmol/L, blood pressure remained 120/80, weight increased to 79 kg, ACTH decreased to 12.1, PTHI increased to 59.9, C-Peptide increased to 4.1, glucose increased to 5.2, Hemoglobin A1C increased to 5.1%, insulin decreased to 11.1.

A male patient of age 39 has the CYP21A2 variant rs6467 CG (global "G" allele frequency G=0.060%), a pseudogene-derived mutation, g.655A/C>G, c.293-13C>G, effect: new splice acceptor, phenotype if homozygous: the classical salt-wasting form of congenital adrenal hyperplasia. No other researched pathogenic variants are found in the gene. The patient presented with chronic bacterial prostatitis. There were leucocytes and bacteria in prostatic secretions. The patient also suffered from hypotension, morning fatigue, brain fog, inability to concentrate, slight intermittent dizziness with nausea, abdominal pain and acne. The analysis results before starting the treatment were the following: 11-deoxycortisol 0.30↓ µg/l (reference range 0.5-3.0), 17-OHP↑ 2.29 ng/mL (reference range 0.5-2.1), progesterone 1.21 nmol/L (reference range 0.159-0.474), SHBG↑ 65.64 nmol/L (reference range 18.3-54.1), ACTH 14.62 pg/mL (reference range 7.2-63.3), PTHI 52.4 pg/mL (reference range 15-65), C-Peptide 2.46 ng/mL (reference range 1.1-4.4), glucose 5.57 mmol/L (reference range 4.1-5.9), Hemoglobin A1C 5.49% (reference range 4-6%), insulin 13.9 µU/mL (reference range 2.6-24.9 µU/mL), GTT 75 g after 2 hours: 4.31 mmol/l, blood pressure↓—90/60, weight—79 kg. After four months of treatment with 0.125 mg of dexamethasone and 10 mg of hydrocortisone daily, the results were the following. Chronic bacterial prostatitis resolved without antibiotics. No leucocytes and no bacteria were found in prostatic secretions. Morning fatigue, dizziness, nausea and abdominal pain resolved, but acne persisted. Blood pressure increased to 120/80. All serum tests were in the normal reference range. 17-OHP decreased to 1.13 ng/mL, progesterone decreased to 0.21 nmol/L, SHBG decreased to 37.33 nmol/L, weight increased to 81 kg, ACTH decreased to 8.93, PTHI decreased to 49.1, C-Peptide increased to 3.81, glucose decreased to 5.01, Hemoglobin A1C remained at 5.49%, insulin decreased to 10.7.

All references, including patents, patent applications and publications cited herein are incorporated herein by reference in their entirety and for all purposes to the same extent as if each individual publication or patent or patent application was specifically and individually indicated to be incorporated by reference in its entirety for all purposes.

REFERENCES

1. Speiser P W, Arlt W, Auchus R J, Baskin L S, Conway G S, Merke D P, Meyer-Bahlburg H F L, Miller W L, Murad M H, Oberfield S E, White P C (2018). "Congenital Adrenal Hyperplasia Due to Steroid 21-Hydroxylase Deficiency: An Endocrine Society Clinical Practice Guideline". The Journal of Clinical Endocrinology and Metabolism. 103 (11): 4043-4088. doi:10.1210/jc.2018-01865. PMC 6456929. PMID 30272171.

2. Turcu A F, Nanba A T, Chomic R, Upadhyay S K, Giordano T J, Shields J J, Merke D P, Rainey W E, Auchus R J (May 2016). "Adrenal-derived 11-oxygenated 19-carbon steroids are the dominant androgens in classic 21-hydroxylase deficiency". European Journal of Endocrinology. 174 (5): 601-9. doi:10.1530/EJE-15-1181. PMC 4874183. PMID 26865584.

3. Merke D P, Auchus R J (September 2020). "Congenital Adrenal Hyperplasia Due to 21-Hydroxylase Deficiency". The New England Journal of Medicine. 383 (13): 1248-1261. doi:10.1056/NEJMra1909786. PMID 32966723.

4. Karachaliou F H, Kafetzi M, Dracopoulou M, Vlachopapadopoulou E, Leka S, Fotinou A, Michalacos S (December 2016). "Cortisol response to adrenocorticotropin testing in nonclassical congenital adrenal hyperplasia (NCCAH)". Journal of Pediatric Endocrinology & Metabolism: JPEM. 29 (12): 1365-1371. doi:10.1515/jpem-2016-0216. PMID 27849625.

5. Chung S, Son G H, Kim K (May 2011). "Circadian rhythm of adrenal glucocorticoid: its regulation and clinical implications". Biochimica Et Biophysica Acta. 1812 (5): 581-91. doi:10.1016/j.bbadis.2011.02.003. PMID 21320597.

6. Adam E K, Quinn M E, Tavernier R, McQuillan M T, Dahlke K A, Gilbert K E (September 2017). "Diurnal cortisol slopes and mental and physical health outcomes: A systematic review and meta-analysis". Psychoneuroendocrinology. 83: 25-41. doi:10.1016/j.psyneuen.2017.05.018. PMC 5568897. PMID 28578301.

7. Dickmeis T (January 2009). "Glucocorticoids and the circadian clock". The Journal of Endocrinology. 200 (1): 3-22. doi:10.1677/JOE-08-0415. PMID 18971218.

8. Koch C E, Leinweber B, Drengberg B C, Blaum C, Oster H (February 2017). "Interaction between circadian rhythms and stress". Neurobiology of Stress. 6: 57-67. doi:10.1016/j.ynstr.2016.09.001. PMC 5314421. PMID 28229109.

9. Nicolaides N C, Charmandari E, Kino T, Chrousos G P (2017). "Stress-Related and Circadian Secretion and Target Tissue Actions of Glucocorticoids: Impact on Health". Frontiers in Endocrinology. 8: 70. doi:10.3389/fendo.2017.00070. PMC 5408025. PMID 28503165.

10. Hindmarsh P C, Honour J W (2020). "Would Cortisol Measurements Be a Better Gauge of Hydrocortisone Replacement Therapy? Congenital Adrenal Hyperplasia as an Exemplar". International Journal of Endocrinology. 2020: 2470956. doi:10.1155/2020/2470956. PMC 7701207. PMID 33299411.

11. Concolino P (October 2019). "Issues with the Detection of Large Genomic Rearrangements in Molecular Diagnosis of 21-Hydroxylase Deficiency". Molecular Diagnosis & Therapy. 23 (5): 563-567. doi:10.1007/s40291-019-00415-z. PMID 31317337.

12. Dimitrakov J, Joffe H V, Soldin S J, Bolus R, Buffington C A, Nickel J C (February 2008). "Adrenocortical hormone abnormalities in men with chronic prostatitis/chronic pelvic pain syndrome". Urology. 71 (2): 261-6. doi:10.1016/j.urology.2007.09.025. PMC 2390769. PMID 18308097.

13. New M I (November 2006). "Extensive clinical experience: non-classical 21-hydroxylase deficiency". The Journal of Clinical Endocrinology and Metabolism. 91 (11): 4205-14. doi:10.1210/jc.2006-1645. PMID 16912124.

14. Speiser P W (March 2009). "Nonclassic adrenal hyperplasia". Reviews in Endocrine & Metabolic Disorders. 10 (1): 77-82. doi:10.1007/s11154-008-9097-x. PMID 18690539. S2CID 30469525.

15. Miller W L, Merke D P (2018). "Tenascin-X, Congenital Adrenal Hyperplasia, and the CAH-X Syndrome". Hormone Research in Paediatrics. 89 (5): 352-361. doi: 10.1159/000481911. PMC 6057477. PMID 29734195

16. Dörr H G, Schulze N, Bettendorf M, Binder G, Bonfig W, Denzer C, et al. (July 2020). "Genotype-phenotype correlations in children and adolescents with non-classical congenital adrenal hyperplasia due to 21-hydroxylase deficiency". Molecular and Cellular Pediatrics. 7 (1): 8. doi: 10.1186/s40348-020-00100-w. PMC 7347723. PMID 32647925

17. Baumgartner-Parzer S, Witsch-Baumgartner M, Hoeppner W (October 2020). "EMQN best practice guidelines for molecular genetic testing and reporting of 21-hydroxylase deficiency". European Journal of Human Genetics. 28 (10): 1341-1367. doi:10.1038/s41431-020-0653-5. PMC 7609334. PMID 32616876. S2CID 220295067.

18. Espinosa Reyes T M, Collazo Mesa T, Lantigua Cruz P A, Agramonte Machado A, Dominguez Alonso E, Falhammar H (November 2020). "Molecular diagnosis of patients with congenital adrenal hyperplasia due to 21-hydroxylase deficiency". BMC Endocrine Disorders. 20 (1): 165. doi:10.1186/s12902-020-00643-z. PMC 7653887. PMID 33168061

19. Tsai W H, Wong C H, Dai S H, Tsai C H, Zeng Y H (2020). "Adrenal Tumor Mimicking Non-Classic Congenital Adrenal Hyperplasia". Frontiers in Endocrinology. 11: 526287. doi:10.3389/fendo.2020.526287. PMC 7551200. PMID 33117272. S2CID 221979120.

20. Homoki J, Teller W M, Fazekas A T (April 1976). "A test for heterozygocity of 21-hydroxylase deficiency: preliminary report". Human Genetics. 32 (1): 35-41. doi: 10.1007/BF00569974. PMID 177352.

21. Halperin G, Finkelstein M (March 1967). "Biosynthesis of pregnanetriolone and pregnanetetrol in congenital adrenal hyperplasia". Acta Endocrinologica. 54 (3): 439-51. doi:10.1530/acta.0.0540439. PMID 6071362.

22. Thomas F J, Steinbeck A W (April 1969). "Quantitative estimation of urinary pregnanetriol, pregnanetriolone, tetrahydro S and delta-5-pregnenetriol in the investigation of adrenocortical function". Acta Endocrinologica. 60 (4): 657-68. doi:10.1530/acta.0.0600657. PMID 5819067.

23. Zachmann M, Prader A (March 1978). "Unusual heterozygotes of congenital adrenal hyperplasia due to 21-hydroxylase deficiency". Acta Endocrinologica. 87 (3): 557-65. doi:10.1530/acta.0.0870557. PMID 580145.

24. Trence D L (September 2003). "Management of patients on chronic glucocorticoid therapy: an endocrine perspective". Primary Care. 30 (3): 593-605. doi:10.1016/s0095-4543(03)00038-1. PMID 14692203.

25. Moghadam-Kia S, Werth V P (March 2010). "Prevention and treatment of systemic glucocorticoid side effects". International Journal of Dermatology. 49 (3): 239-48. doi:10.1111/j.1365-4632.2009.04322.x. PMC 2872100. PMID 20465658.

26. Whittle E, Falhammar H (June 2019). "Glucocorticoid Regimens in the Treatment of Congenital Adrenal Hyperplasia: A Systematic Review and Meta-Analysis". Journal of the Endocrine Society. 3 (6): 1227-1245. doi:10.1210/js.2019-00136. PMC 6546346. PMID 31187081.

27. Ng S M, Stepien K M, Krishan A (March 2020). "Glucocorticoid replacement regimens for treating congenital adrenal hyperplasia". The Cochrane Database of Systematic Reviews. 3: CD012517. doi:10.1002/14651858.CD012517.pub2. PMC 7081382. PMID 32190901.

28. Thunhorst R L, Beltz T G, Johnson A K (September 2007). "Glucocorticoids increase salt appetite by promoting water and sodium excretion". American Journal of Physiology. Regulatory, Integrative and Comparative Physiology. 293 (3): R1444-51. doi:10.1152/ajpregu.00294.2007. PMC 2922067. PMID 17596327.

29. Matthews D, Cheetham T (March 2013). "What is the best approach to the teenage patient presenting with non-classical congenital adrenal hyperplasia: should we always treat with glucocorticoids?". Clinical Endocrinology. 78 (3): 338-41. doi:10.1111/cen.12065. PMID 23039910.

30. Sumińska M, Bogusz-Górna K, Wegner D, Fichna M (June 2020). "Non-Classic Disorder of Adrenal Steroidogenesis and Clinical Dilemmas in 21-Hydroxylase Deficiency Combined with Backdoor Androgen Pathway. Mini-Review and Case Report". International Journal of Molecular Sciences. 21 (13): 4622.

31. Witchel S F, Azziz R (2010). "Nonclassic congenital adrenal hyperplasia". International Journal of Pediatric Endocrinology. 2010: 625105. doi:10.1155/2010/625105. PMC 2910408. PMID 20671993.

32. Auchus R J (November 2004). "The backdoor pathway to dihydrotestosterone". Trends in Endocrinology and Metabolism. 15 (9): 432-8. doi:10.1016/j.tem.2004.09.004. PMID 15519890. S2CID 10631647.

33. Pignatelli, Duarte; Pereira, Sofia S.; Pasquali, Renato (2019). "Androgens in Congenital Adrenal Hyperplasia". Hyperandrogenism in Women. Frontiers of Hormone Research. 53. pp. 65-76. doi:10.1159/000494903. ISBN 978-3-318-06470-4. PMID 31499506.

34. Turcu A F, Rege J, Auchus R J, Rainey W E (May 2020). "11-Oxygenated androgens in health and disease". Nature Reviews. Endocrinology. 16 (5): 284-296. doi:10.1038/s41574-020-0336-x. PMID 32203405. S2CID 212732699.

35. Barnard L, Nikolaou N, Louw C, Schiffer L, Gibson H, Gilligan L C, Gangitano E, Snoep J, Arlt W, Tomlinson J W, Storbeck K H (September 2020). "The A-ring reduction of 11-ketotestosterone is efficiently catalysed by AKR1D1 and SRD5A2 but not SRD5A1". The Journal of Steroid Biochemistry and Molecular Biology. 202: 105724. doi:10.1016/j.jsbmb.2020.105724. PMID 32629108. S2CID 220323715.

36. Turcu A F, Mallappa A, Elman M S, Avila N A, Marko J, Rao H, Tsodikov A, Auchus R J, Merke D P (August 2017). "11-Oxygenated Androgens Are Biomarkers of Adrenal Volume and Testicular Adrenal Rest Tumors in 21-Hydroxylase Deficiency". The Journal of Clinical Endocrinology and Metabolism. 102 (8): 2701-2710.

37. White P C (June 2018). "Update on diagnosis and management of congenital adrenal hyperplasia due to 21-hydroxylase deficiency". Current Opinion in Endocrinology, Diabetes and Obesity. 25 (3): 178-184. doi:10.1097/MED 0000000000000402. PMID 29718004. S2CID 26072848.

38. Nagasaki, Keisuke; Takase, Kaoru; Numakura, Chikahiko; Homma, Keiko; Hasegawa, Tomonobu; Fukami, Maki (30 Aug. 2020). "Foetal virilisation caused by overproduction of non-aromatisable 11-oxygenated C19 steroids in maternal adrenal tumour". Human Reproduction: deaa221. doi:10.1093/humrep/deaa221. PMID 32862221.

39. Barnard L, Schiffer L, Louw du-Toit R, Tamblyn J A, Chen S, Africander D, Arlt W, Foster P A, Storbeck K H (March 2021). "11-Oxygenated Estrogens Are a Novel Class of Human Estrogens but Do not Contribute to the Circulating Estrogen Pool". Endocrinology. 162 (3). doi:10.1210/endocr/bqaa231. PMC 7814299. PMID 33340399.

40. Verbeeten K C, Ahmet A H (January 2018). "The role of corticosteroid-binding globulin in the evaluation of adrenal insufficiency". Journal of Pediatric Endocrinology & Metabolism: JPEM. 31 (2): 107-115. doi:10.1515/jpem-2017-0270. PMID 29194043. S2CID 28588420.

41. Izawa S, Sugaya N, Ogawa N, Shirotsuki K, Nomura S (April 2021). "A validation study on fingernail cortisol: correlations with one-month cortisol levels estimated by hair and saliva samples". Stress (Amsterdam, Netherlands): 1-8. doi:10.1080/10253890.2021.1895113. PMID 33792492.

42. Turpeinen U, Hämäläinen E (December 2013). "Determination of cortisol in serum, saliva and urine". Best Practice & Research. Clinical Endocrinology & Metabolism. 27 (6): 795-801. doi:10.1016/j.beem.2013.10.008. PMID 24275191.

43. Dolomie-Fagour L, CorcuffJB (2008). "[Is free plasmatic cortisol measurement useful in intensive care unit?]". Annales De Biologie Clinique (in French). 66 (1): 31-41. doi:10.1684/abc.2008.0189. PMID 18227002.

44. Maidana P, Bruno O D, Mesch V (2013). "[A critical analysis of cortisol measurements: an update]". Medicina (in Spanish; Castilian). 73 (6): 579-84. PMID 24356273.

45. Winter W E, Bazydlo L, Harris N S (2012). "Cortisol—Clinical Indications and Laboratory Testing". AACC Clinical Laboratory News. Archived from the original on 2018-01-04.

46. Krasowski M D, Drees D, Morris C S, Maakestad J, Blau J L, Ekins S (2014). "Cross-reactivity of steroid hormone immunoassays: clinical significance and two-dimensional molecular similarity prediction". BMC Clinical Pathology. 14 (33): 33. doi:10.1186/1472-6890-14-33. PMC 4112981. PMID 25071417.

47. Agrawal, N.; Chakraborty, P. P.; Sinha, A.; Maiti, A. (2020). "False elevation of serum cortisol in chemiluminescence immunoassay by Siemens Advia Centaur XP system in 21-hydroxylase deficiency: An 'endocrine laboma'". BMJ Case Reports. 13 (9): e235450. doi:10.1136/bcr-2020-235450. PMC 7477984. PMID 32900728. S2CID 221567576.

48. Kurtoglu, Selim; Hatipoglu, Nihal (7 Mar. 2017). "Non-classical Congenital Adrenal Hyperplasia in Childhood". Journal of Clinical Research in Pediatric Endocrinology. 9 (1): 1-7. doi:10.4274/jcrpe.3378. PMC 5363159. PMID 27354284.

49. Hawley J M, Keevil B G (September 2016). "Endogenous glucocorticoid analysis by liquid chromatography-tandem mass spectrometry in routine clinical laboratories". The Journal of Steroid Biochemistry and Molecular Biology. 162: 27-40. doi:10.1016/j.jsbmb.2016.05.014. PMID 27208627. S2CID 206501499.

50. D'aurizio F, Cantu M (September 2018). "Clinical endocrinology and hormones quantitation: the increasing role of mass spectrometry". Minerva Endocrinologica. 43 (3): 261-284. doi:10.23736/50391-1977.17.02764-X. PMID 29083134.

51. Meinders A J, Meinders A E (2010). "[How much water do we really need to drink?]". Nederlands Tijdschrift Voor Geneeskunde (in Dutch; Flemish). 154: A1757. PMID 20356431.

52. Fuqua J S, Rogol A D (July 2013). "Neuroendocrine alterations in the exercising human: implications for energy homeostasis". Metabolism. 62 (7): 911-21. doi:10.1016/j.metabol.2013.01.016. PMID 23415825.

53. Arshad M F, Debono M (March 2021). "Current and future treatment options for adrenal insufficiency". Current Opinion in Endocrinology, Diabetes, and Obesity. doi:10.1097/MED.0000000000000637. PMID 33782339.

54. Valtin H (November 2002). "Drink at least eight glasses of water a day." Really? Is there scientific evidence for "8×8"?". American Journal of Physiology. Regulatory, Integrative and Comparative Physiology. 283 (5): R993-1004. doi:10.1152/ajpregu.00365.2002. PMID 12376390.

55. Thornton S N (December 2012). "Thirst drives us to drink at least two litres of water a day". Australian and New Zealand Journal of Public Health. 36 (6): 585. doi:10.1111/j.1753-6405.2012.00938.x. PMID 23216505.

56. Falhammar H, Wedell A, Nordenstrom A (November 2015). "Biochemical and genetic diagnosis of 21-hydroxylase deficiency". Endocrine. 50 (2): 306-14. doi:10.1007/s12020-015-0731-6. PMID 26336836.

57. Falhammar H, Nordenstrom A (September 2015). "Nonclassic congenital adrenal hyperplasia due to 21-hydroxylase deficiency: clinical presentation, diagnosis, treatment, and outcome". Endocrine. 50 (1): 32-50. doi:10.1007/s12020-015-0656-0. PMID 26082286.

58. AU 2015209452, C1, 04.08.2016.

59. AU 2020207774, A1, 06.08.2020.

60. CA 2936974, A1, 30.07.2015.

61. CN 106102740, A, 09.11.2016.

62. CN 111228274, A, 05.06.2020.
63. EP3096756, A1, 30.11.2016.
64. IL246783, A, 31.08.2016.
65. IN201617026877, A, 1.08.2016.
66. JP2017503030, B2, 26.01.2017.
67. JP2019081814, A, 30.05.2019.
68. JP2020138978, A, 03.09.2020.
69. KR1020160106176, A, 09.09.2016.
70. MX2016009499, A, 27.02.2017.
71. NZ722122, B2, 26.06.2020.
72. RU0002718918, C2, 15.04.2020.
73. RU2020112197, A, 21.05.2020.
74. US20170020877, A1, 26.01.2017.
75. US20190231781, B2, 02.02.2021.
76. WO2015112642, B2, 02.02.2021.
77. WO2021016208, B2, 28.01.2021.

What is claimed is:

1. A method of treating a patient with late-onset congenital adrenal hyperplasia due to 21-hydroxylase deficiency caused by a mutation in the CYP21A2 gene comprising:
    administering, to the patient, daily doses of glucocorticoids comprising:
        a dose of a short-acting glucocorticoid comprising hydrocortisone in the morning; and
        a dose of a long-acting glucocorticoid comprising dexamethasone in the evening,
        wherein the doses are optimized for the patient to counterbalance adverse reactions;
    measuring a serum level of sex hormone binding globulin (SHBG) of the patient; and
    adjusting the daily doses of the glucocorticoids based on the measured serum level of SHBG, wherein said adjusting comprises:
        decreasing the dose of the long-acting glucocorticoid if the serum level of SHBG has reached a level of less than 120 nmol/L for women, or less than 49 nmol/L for men under 50 years of age, or less than 70 nmol/L for men over 50 years of age, otherwise the daily dose of dexamethasone is increased.

2. The method of claim 1, wherein the dose of the short-acting glucocorticoid is from 5 mg to 30 mg and the dose of the long-acting glucocorticoid is from 0.05 mg to 0.75 mg.

3. The method of claim 2, wherein the dose of the short-acting glucocorticoid is 10 mg.

4. The method of claim 3, wherein the dose of the long-acting glucocorticoid is 0.25 mg.

5. The method of claim 1, wherein the dose of the long-acting glucocorticoid is 0.25 mg.

6. The method of claim 1, wherein the daily doses of glucocorticoids are further adjusted based on results of analyzes of one or more of: blood pressure, body weight, serum levels of 17α-hydroxyprogesterone (17-OHP), progesterone, adrenocorticotropic hormone (ACTH), serum glucose, glycated hemoglobin (HbA1c), C-peptide, intact parathyroid hormone (PTH) and insulin.

7. The method of claim 1, wherein said adjusting of the glucocorticoid doses is performed monthly.

8. The method of claim 1, wherein said adjusting further comprises:
    decreasing the daily dose of the long-acting glucocorticoid if a serum level of 17-OHP has reached a level of less than 0.8 ng/mL for women in a follicular phase of a menstrual cycle or less than 0.5 ng/mL for postmenopausal women or less than 1.6 ng/mL for men, otherwise the daily dose is increased.

9. The method of claim 1, wherein said adjusting further comprises:
    decreasing the daily dose of the long-acting glucocorticoid if a serum progesterone level has reached a level of less than 2.7 nmol/L for women in a follicular phase of the menstrual cycle, or less than 0.3 nmol/L for postmenopausal women, or less than 0.4 nmol/L for men, otherwise the daily dose is increased.

10. The method of claim 1, further comprising:
    upon detecting swelling, edema or hypertension, decreasing a daily sodium intake of the patient to up to 400 mg of elemental sodium.

11. The method of claim 1, further comprising:
    upon determining that a blood pressure of the patient is low, in the absence of edema, increasing a daily sodium intake to 2000 mg of elemental sodium.

12. The method of claim 1, wherein said adjusting further comprises:
    decreasing the daily dose of the short-acting glucocorticoid upon detecting swelling, edema or hypertension.

13. The method of claim 1, further comprising providing a dietary supplement comprising 4 g of elemental potassium to the patient.

14. The method of claim 1, further comprising providing a daily dietary supplement comprising 1.4 g of elemental calcium to the patient.

15. The method of claim 1, further comprising providing a daily vitamin supplement comprising 1,000 IU of vitamin D3 to the patient.

16. The method of claim 1, further comprising providing a daily vitamin supplement comprising 150 mcg of vitamin K to the patient.

* * * * *